United States Patent [19]

Yamatsu et al.

[11] Patent Number: 4,522,759

[45] Date of Patent: Jun. 11, 1985

[54] POLYPRENYLCARBOXYLIC ACID AMIDES

[75] Inventors: Isao Yamatsu; Takeshi Suzuki, both of Ushikumachi; Shinya Abe, Kukisaki; Akiharu Kajiwara, Ibaragi; Kiichiro Ota, Wakayama, all of Japan

[73] Assignee: Eisai Co., Ltd., Tokyo, Japan

[21] Appl. No.: 484,111

[22] Filed: Apr. 11, 1983

[30] Foreign Application Priority Data

Apr. 13, 1982 [JP] Japan .................................. 57-60310

[51] Int. Cl.³ ........................ C11C 3/00; A61K 31/165
[52] U.S. Cl. ...................................... 260/404; 514/821; 514/826; 514/854; 514/886; 514/921; 560/39
[58] Field of Search ................ 260/404; 424/324, 309; 560/39

[56] References Cited

U.S. PATENT DOCUMENTS

| | | | |
|---|---|---|---|
| 4,053,509 | 10/1977 | Faro et al. ....................... | 260/404 X |
| 4,115,587 | 9/1978 | Lunsford et al. ................ | 260/404 X |
| 4,275,219 | 6/1981 | Zupan ............................. | 260/404 X |
| 4,337,207 | 6/1982 | Goodman et al. .............. | 260/404 X |
| 4,402,981 | 9/1983 | Liepmann et al. ...... | 260/404.5 R X |

FOREIGN PATENT DOCUMENTS 87136  8/1983  European Pat. Off. ............ 260/404

Primary Examiner—Thomas A. Waltz
Attorney, Agent, or Firm—Flynn, Thiel, Boutell and Tanis

[57] ABSTRACT

There is disclosed a polyprenylcarboxylic acid amide of the formula:

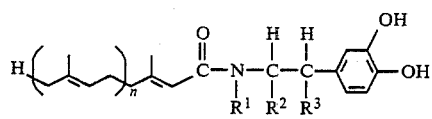

wherein $R^1$ represents a hydrogen atom or a lower alkyl group, $R^2$ represents a hydrogen atom or a group of the formula: $-COOR^4$ in which $R^4$ represents a lower alkyl group, $R^3$ represents a hydrogen atom or an OH group and n represents an integer of 1 to 6.

6 Claims, 8 Drawing Figures

POLYPRENYLCARBOXYLIC ACID AMIDES

The present invention is related to a polyprenylcarboxylic acid amide, called also a polyprenoic acid amide, which is useful as a medicine and a process for preparing the same. More in particular, the present invention relates to polyprenylcarboxylic acid amides of the general formula:

wherein $R^1$ represents a hydrogen atom or a lower alkyl group, $R^2$ represents a hydrogen atom or a group of the formula: —$COOR^4$ in which $R^4$ represents a lower alkyl group, $R^3$ represents a hydrogen atom or an OH group and n represents an integer of 1 to 6, and a process for preparing them.

The lower alkyl groups in the definitions of $R^1$, $R^2$ and $R^4$ in the above general formula [I] are straight-chain or branched alkyl groups having 1 to 6 carbon atoms, such as methyl, ethyl, n-propyl, isopropyl, n-butyl, isobutyl, 1-methylpropyl, tert-butyl, n-pentyl, 1-ethylpropyl, isoamyl and n-hexyl group.

The polyprenylcarboxylic acid amides provided by the present invention are novel compounds not disclosed yet in the literature. They have excellent physiological effects and are highly valuable as medicines.

The compounds of the present invention are derivatives of catecholamines such as dopamine, L-dopa, epinephrine, norepinephrine and isoproterenol. The compounds exhibit the physiological effects of these catecholamines for a long time.

According to the inventors' experiments, they have a remarkable cyclic AMP-increasing effect, a long-lasting PTH (parathormone) secreting effect and a lasting $\beta_2$-agonistic effect.

Therefore, like norepinephrine and epinephrine, the compounds of the present invention are useful as adrenergic agents for the treatment or prevention of allergic diseases such as asthma, nasitis and hives and also as a vasoconstrictor, hypotension remedy, cardiotonic drug, shock remedy and thrombopathy remedy. Further, they are also useful as remedies based on their cyclic AMP-increasing and lasting PTH secretion effects.

Typical examples of the compounds of the present invention are as follows, which by no means limit the invention:

N-(3,7-dimethyl-2,6-octadienoyl)dopamine,
N-(3,7,11-trimethyl-2,6,10-dodecatrienoyl)dopamine,
N-(3,7,11,15-tetramethyl-2,6,10,14-hexadecatetraenoyl)dopamine,
N-(3,7,11,15,19-pentamethyl-2,6,10,14,18-eicosapentaenoyl)dopamine,
N-(3,7,11,15,19,23-hexamethyl-2,6,10,14,18,22-tetracosahexaenoyl)dopamine,
N-(3,7,11,15,19,23,27-heptamethyl-2,6,10,14,18,22,26-octacosaheptaenoyl)dopamine,
methyl-N-(3,7-dimethyl-2,6-octadienoyl)-L-dopa,
methyl-N-(3,7,11-trimethyl-2,6,10-dodecatrienoyl)-L-dopa,
methyl-N-(3,7,11,15-tetramethyl-2,6,10,14-hexadecatetraenoyl)-L-dopa,
methyl-N-(3,7,11,15,19-pentamethyl-2,6,10,14,18-eicosapentaenoyl)-L-dopa,
methyl-N-(3,7,11,15,19,23-hexamethyl-2,6,10,14,18,22-tetracosahexaenoyl)-L-dopa,
methyl-N-(3,7,11,15,19,23,27-heptamethyl-2,6,10,18,22,26-octacosaheptaenoyl)-L-dopa,
N-(3,7-dimethyl-2,6-octadienoyl)-l-epinephrine,
N-(3,7,11-trimethyl-2,6,10-dodecatrienoyl)-l-epinephrine,
N-(3,7,11,15-tetramethyl-2,6,10,14-hexadecatetraenoyl)-l-epinephrine,
N-(3,7,11,15,19-pentamethyl-2,6,10,14,18-eicosapentaenoyl)-l-epinephrine,
N-(3,7,11,15,19,23-hexamethyl-2,6,10,14,18,22-tetracosahexaenoyl)-l-epinephrine,
N-(3,7,11,15,19,23,27-heptamethyl-2,6,10,14,18,22,26-octacosaheptaenoyl)-l-epinephrine,
N-(3,7-dimethyl-2,6-octadienoyl)-l-norepinephrine,
N-(3,7,11-trimethyl-2,6,10-dodecatrienoyl)-l-norepinephrine,
N-(3,7,11,15-tetramethyl-2,6,10,14-hexadecatetraenoyl)-l-norepinephrine,
N-(3,7,11,15,19-pentamethyl-2,6,10,14,18-eicosapentaenoyl)-l-norepinephrine,
N-(3,7,11,15,19,23-hexamethyl-2,6,10,14,18,22-tetracosahexaenoyl)-l-norepinephrine,
N-(3,7,11,15,19,23,27-heptamethyl-2,6,10,14,18,22,26-octacosaheptaenoyl)-l-norepinephrine,
N-(3,7-dimethyl-2,6-octadienoyl)-dl-isoproterenol,
N-(3,7,11-trimethyl-2,6,10-undecatrienoyl)-dl-isoproterenol,
N-(3,7,11,15-tetramethyl-2,6,10,14-hexadecatetraenoyl)-dl-isoproterenol,
N-(3,7,11,15,19-pentamethyl-2,6,10,14,18-eicosapentaenoyl)-dl-isoproterenol,
N-(3,7,11,15,19,23-hexamethyl-2,6,10,14,18,22-tetracosahexaenoyl)-dl-isoproterenol, and
N-(3,7,11,15,19,23,27-heptamethyl-2,6,10,14,18,22,26-octacosaheptaenoyl)-dl-isoproterenol.

Compounds [I] of the present invention can be prepared by various processes. An example of generally employed processes will be given below.

A polyprenylcarboxylic acid of the general formula [II]:

wherein n represents an integer of 1 to 6, or a reactive derivative thereof is reacted with an amino compound of the general formula [III]:

wherein $R^1$ represents a hydrogen atom or a lower alkyl group, $R^2$ represents a hydrogen atom or a group of the formula: —$COOR^4$ in which $R^4$ represents a lower alkyl group, $R^3$ represents a hydrogen atom or a group of the formula —OH.

As the reactive derivatives of the polyprenylcarboxylic acids, there may be mentioned, for example, acid chlorides, acid anhydrides and acid azides. The reactive derivatives are not necessarily isolated nor purified and they may be used in the form of a reaction mixture for the reaction with the amino compounds. The reaction is carried out generally in the presence of a base such as triethylamine or dimethylaniline in an organic solvent such as acetone, ether, tetrahydrofuran, dioxane, dimethylformamide, hexamethylphosphoric triamide (HMPA), chloroform or dichloromethane or a mixture of these solvents or a mixture of these solvents with water at room temperature or under cooling.

Polyprenylcarboxylic acids [II] used as the starting material in the above-mentioned process are obtained by, for example, reacting a polyprenyl ketone of the general formula [IV]:

[IV]

wherein n has the same meaning as above, with, for example, triethyl phosphonoacetate in the presence of a base to form an ethyl ester of the general formula [V]:

[V]

wherein n has the same meaning as above, and hydrolyzing the ethyl ester with, for example, a base such as KOH to form the polyprenylcarboxylic acid of the general formula [II].

BRIEF DESCRIPTION OF DRAWINGS

The ordinates show the PTH concentration and the abscissae show the concentration of the compound of the present invention.

The ordinates show the PTH concentration and the abscissae show the time (min). The solid line shows changes in the PTH secretion effect with time observed when the compound of the present invention ($10^{-5}$M) was used and the dotted line shows those observed when a control was used.

The ordinates show the concentration of PTH and the abscissae show the amount of epinephrine.

The ordinates show the concentration of PTH and the abscissae show the amount of the compound of the present invention.

The ordinates show the concentration of PTH and the abscissae show the amount of the compound of the present invention.

The ordinates show the concentration of cyclic AMP in the blood plasma and the abscissae show the amount of the compound of the present invention.

The ordinates show the concentration of cyclic AMP in the blood plasma and the abscissae show the amount of the compound of the present invention.

Excellent physiological effects of typical compounds of the present invention will be illustrated below.

EXPERIMENTS

PTH (parathormone) secretion and cyclic AMP-increasing effects (1) Method of experiments A test compound was dissolved in lecithin liposome and 150 μl in total of the sample was injected into femoral veins of Wistar rats weighing 150 g after fasting for 24 h. 1 and 5 min after the injection, the blood was taken from the abdominal main artery. 50 μl of 500 mM EDTA (pH 7.45) was charged in a test tube and then 3 ml of the blood from the abdominal main artery was added thereto. After stirring, the mixture was centrifuged in a refrigerated centrifuge at 2,000 rpm for 10 min. The blood plasma was taken. PTH and cyclic AMP contained in the blood plasma were determined. PTH was determined by means of radioimmunoassay.

As the test compound, N-(3,7,11,15-tetramethyl-2,6,10,14-hexadecatetraenoyl)-l-epinephrine was used.

(2) Results

The results are shown in FIGS. 1 to 8.

Figure 1:
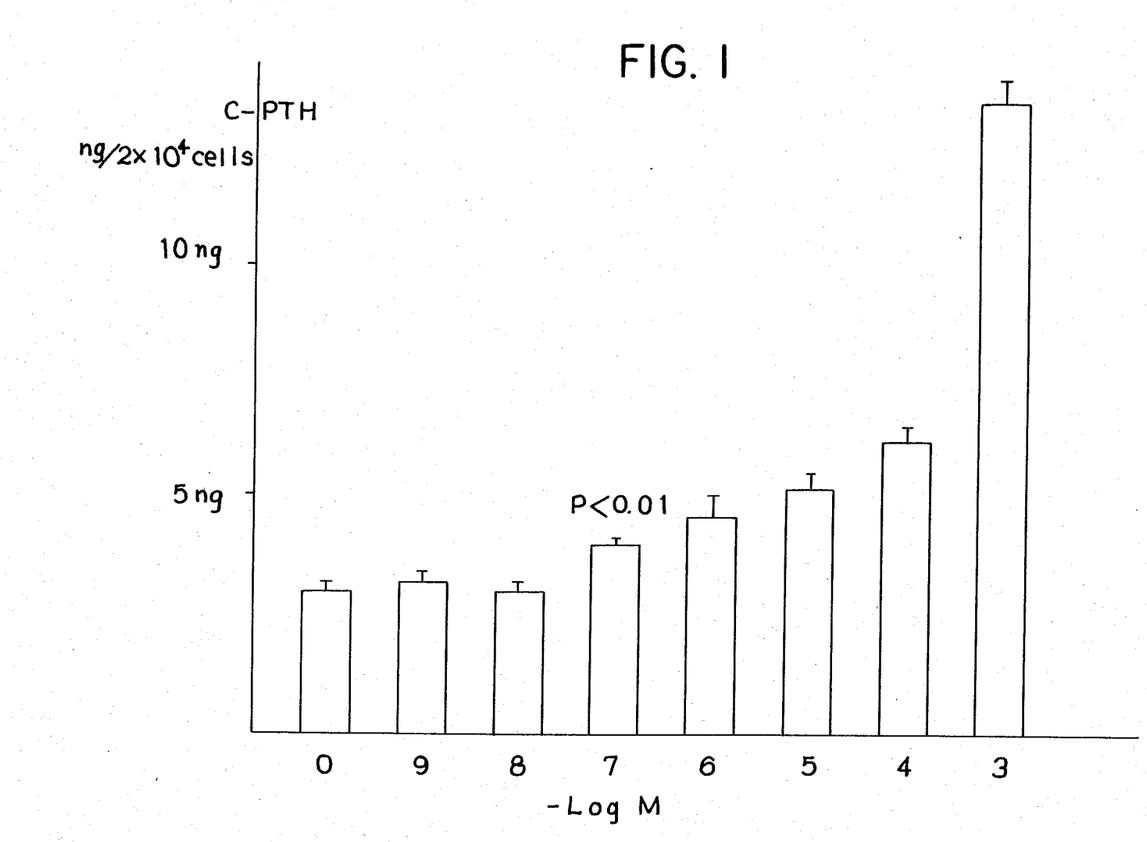
FIG. 1 shows a PTH secretion effect of the compound of the present invention in bovine parathyroid cells.

FIG. 1 shows the results of the examination of PTH secretion in bovine parathyroid cells carried out by preparing a concentration gradient of the test compound with a solubilizer. The abscissae show the concentration of the test compound and the ordinates show the amount of PTH.

It is apparent from FIG. 1 that PTH is secreted in proportion to the amount of the test compound in the concentration range of $10^{-7}$ to $10^{-3}$M.

Figure 2:
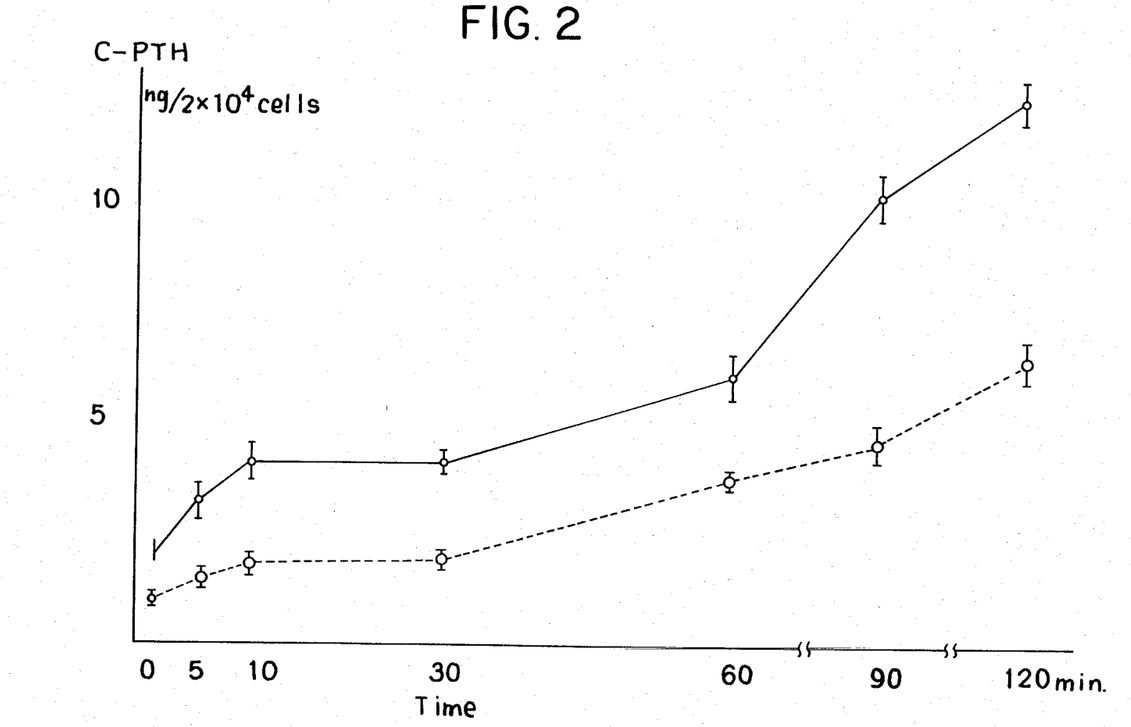
FIG. 2 shows changes in the PTH secretion effect of the compound of the present invention ($10^{-5}$M) with time in bovine parathyroid cells.

FIG. 2 shows the results of the examination of PTH secretion with time carried out by using parathyroid cells with a test compound concentration of $10^{-5}$M. The abscissae show the time (min) and the ordinates show the amount of PTH.

Figure 3:
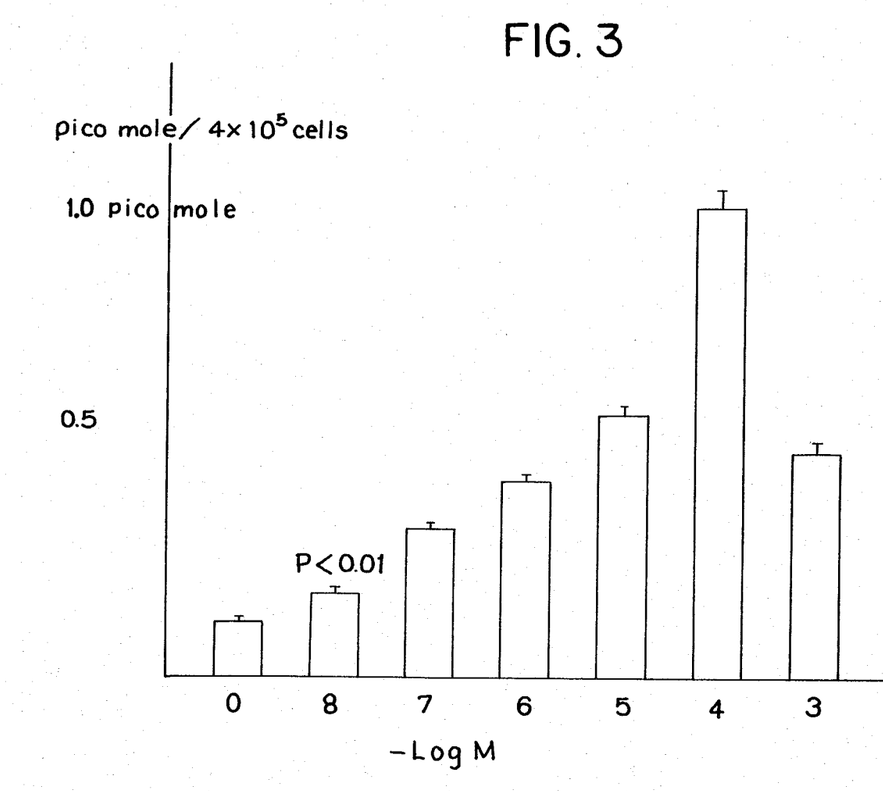
FIG. 3 shows a cyclic AMP-increasing effect of the compound of the present invention in bovine parathyroid cells. The ordinates show the amount of cyclic AMP and abscissae show the concentration of the compound of the present invention.

FIG. 3 shows the results of the examination of release of cyclic AMP in the culture liquid of parathyroid cells carried out by preparing a concentration gradient of the test compound. The abscissae show the concentration of the test compound and the ordinates show the amount of cyclic AMP.

It is apparent from FIG. 3 that cyclic AMP was released from the parathyroid cells in proportion to the amount of the test compound in a concentration range of up to $10^{-4}$M.

Figure 4:
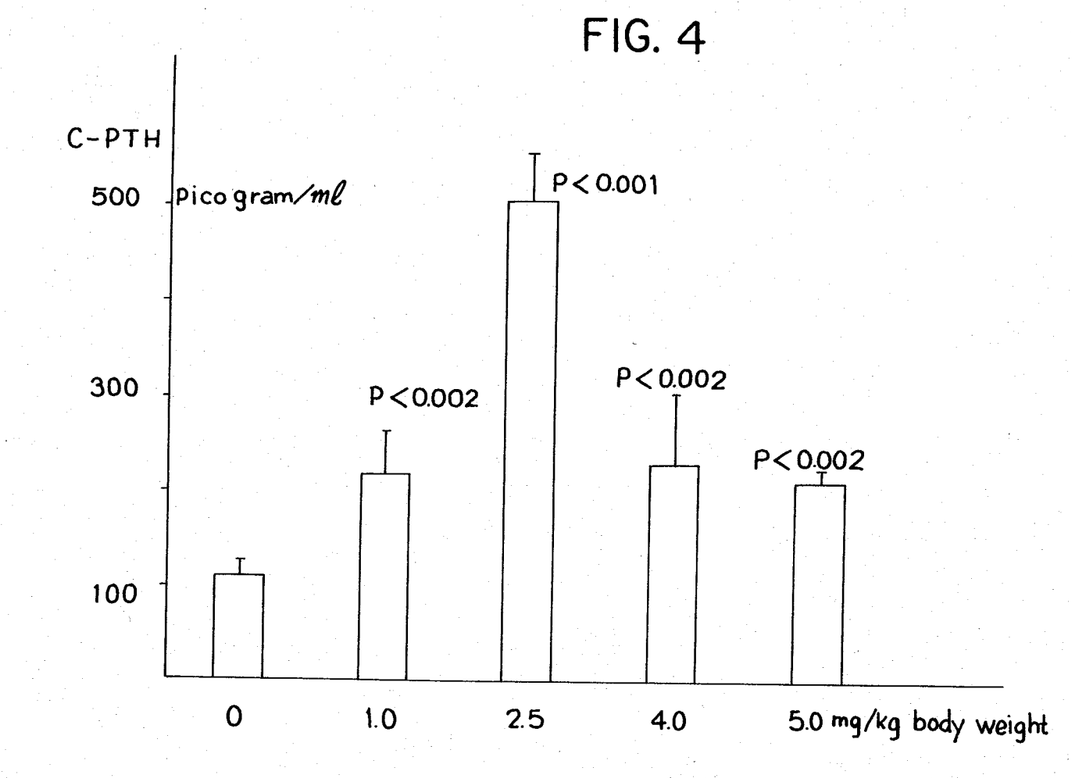
FIG. 4 shows the effect of epinephrine on PTH in the blood plasma.

FIG. 4 shows the results of the examination of the amount of PTH in blood plasma obtained carried out by injecting 1.0 to 5.0 mg/kg-body weight of Wistar male rats of epinephrine into femoral veins of the rats. The abscissae show the concentration of epinephrine and the ordinates show the amount of PTH.

It is apparent from FIG. 4 that the maximum PTH secretion was obtained with 2.5 mg/kg-body weight of epinephrine. With a higher concentration of epinephrine, the secretion was rather inhibited.

Figure 5:
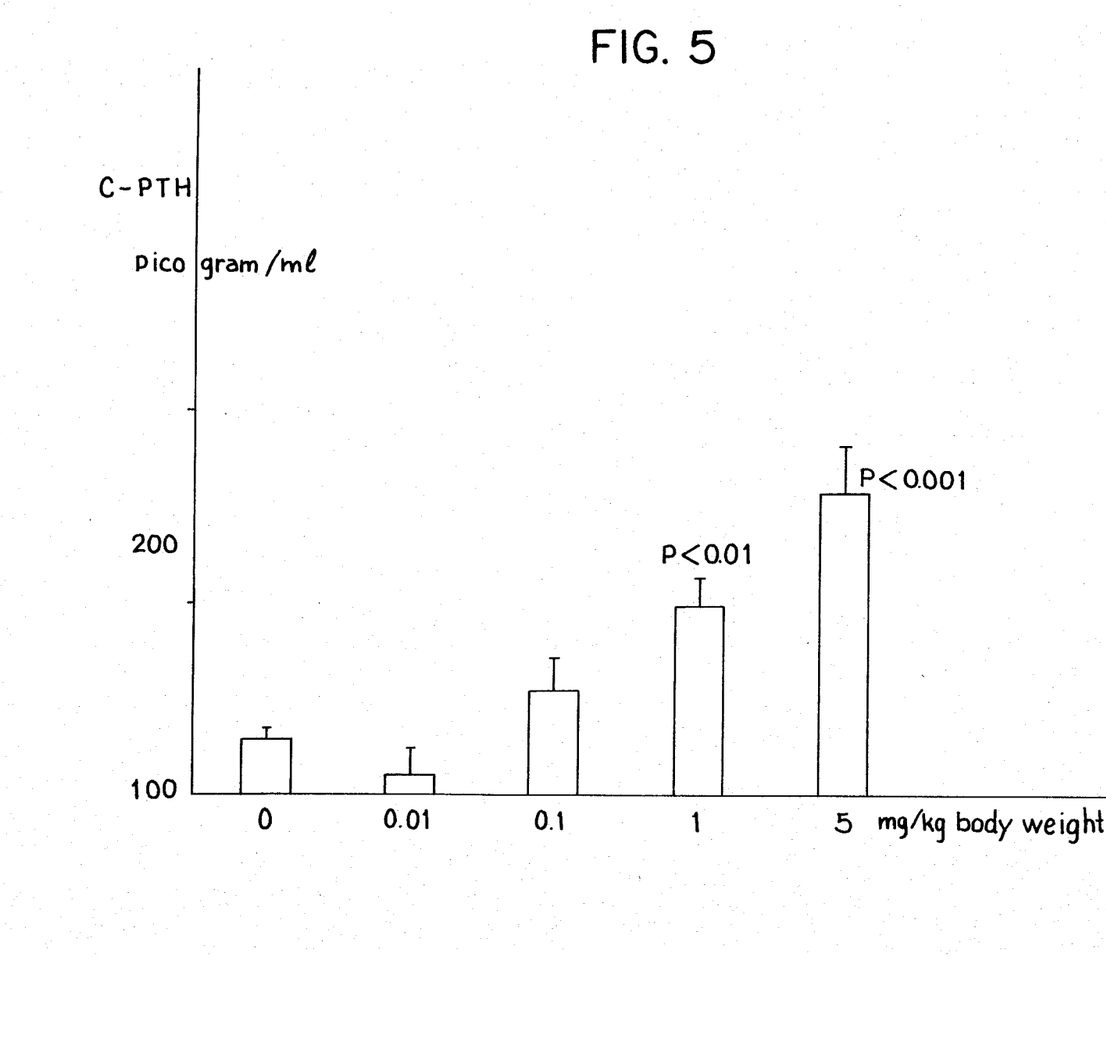
FIG. 5 shows PTH increase in the blood plasma observed 5 min after the administration of the compound of the present invention to rats.

FIG. 5 shows the results obtained by injecting 0.01, 0.1, 1 and 5 mg/kg-body weight of the test compound into Wistar male rats weighing 150 g and examining PTH in the blood plasma after 5 min. The abscissae show the concentration of the test compound and the ordinates show the amount of PTH.

It is apparent from FIG. 5 that PTH in the blood plasma was increased in proportion to the amount of the test compound in the range of 0.1 to 5 mg/kg.

Figure 6:
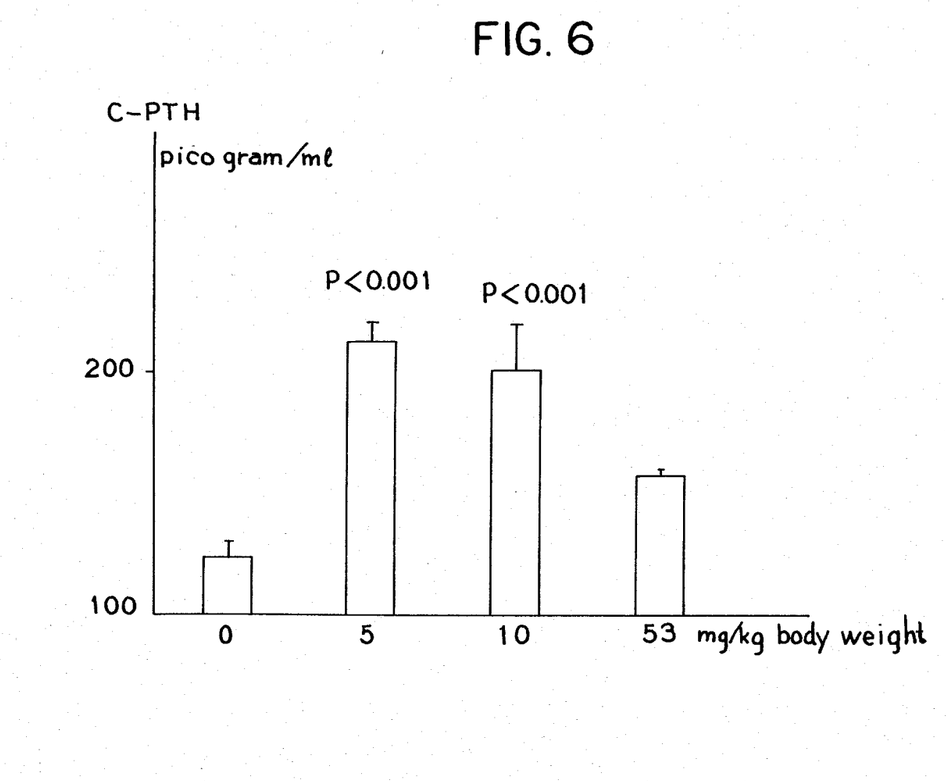
FIG. 6 shows PTH increase in the blood plasma observed 1 min after the administration of the compound of the present invention to rats.

FIG. 6 shows the results obtained by administering 5, 10 and 53 mg/kg of the test compound by intravenous injection to Wistar male rats weighing 150 g and examining blood plasma PTH after one min. The abscissae show the concentration of the test compound and the ordinates show the amount of PTH.

It is apparent from FIG. 6 that the maximum secretion was observed when 5 or 10 mg/kg-body weight of the test compound was injected into the rats.

Figure 7:
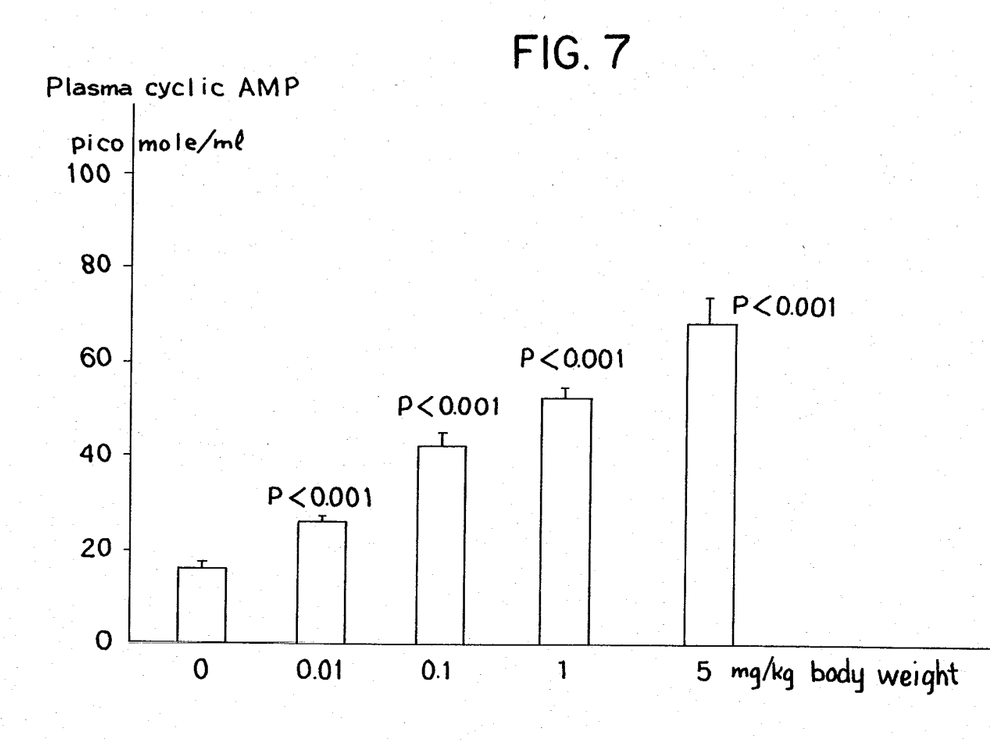
FIG. 7 shows cyclic AMP increase in the blood plasma observed 5 min after the administration of the compound of the present invention to rats.

FIG. 7 shows the results of the examination of influences of 0.01, 0.1, 1 and 5 mg/kg-body weight of the test compound on cyclic AMP in the blood plasma of Wistar male rats weighing 150 g 5 min after the injection. The abscissae show the concentration of the test compound and the ordinates show the amount of cyclic AMP.

It is apparent from FIG. 7 that cyclic AMP in the blood plasma was increased in proportion to the concentration of the test compound in the range of 0.01 to 5 mg/kg.

Figure 8:
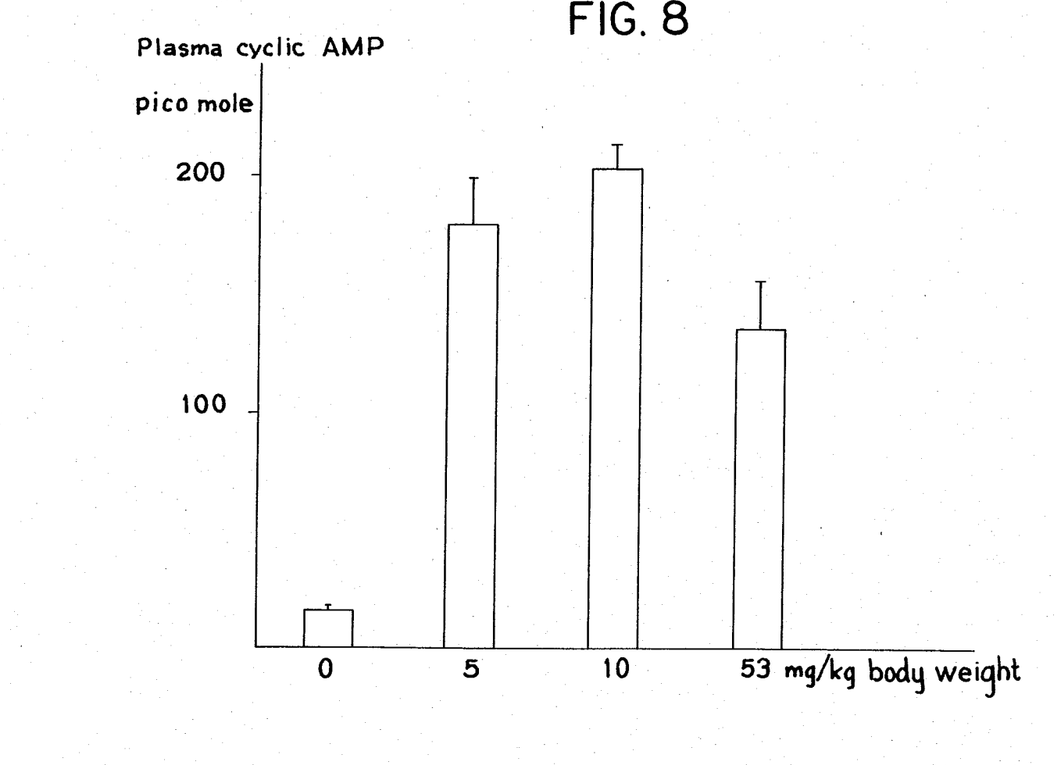
FIG. 8 shows cyclic AMP increase in the blood plasma observed 1 min after the administration of the compound of the present invention to rats.

FIG. 8 shows the results of examination obtained by injecting 5, 10 and 53 mg/kg-body weight of the test compound into Wistar male rats weighing 150 g and examining influences thereof on cyclic AMP in the blood plasma one min after the injection.

It is apparent from FIG. 8 that the maximum cyclic AMP releasing effect in blood plasma was obtained with 10 mg/kg-body weight of the test compound.

(3) Conclusion

It is apparent from the above experimental results that effects of the test compound on PTH secretion and cyclic AMP release obtained by using bovine parathyroid cells were in proportion to the amount of the compound and that the PTH secretion lasted for a long time. This fact indicates that the compound of the present invention has a continuous PTH-secreting effect, while epinephrine has a pulse-like PTH secretion effect.

In the experiments using rats, the test compound exhibited a blood plasma cyclic AMP-increasing effect.

It is apparent from the above experiments that the compound of the present invention has remarkable cyclic AMP-increasing and continuous PTH secretion effects. The compound is usable or an adrenergic agent for the treatment or prevention of allergic diseases such as asthma, nasitis and hives and also as a local vasoconstrictor, hypotension remedy, cardiotonic drug, shock remedy and thrombopathy remedy. The compound is thus quite valuable.

The compounds of the present invention are used in the form of tablets, granules, powders, capsules, injections and suppositories prepared by ordinary methods employed in the art.

In preparing an oral solid preparation, an excipient and, if necessary, a binder, disintegrator, lubricant, colorant and corrigent are added to the active ingredient and then the mixture is shaped into tablets, coated tablets, granules, powders or capsules by an ordinary method.

As the excipients, there may be used, for example, lactose, corn starch, white sugar, sorbitol, crystalline cellulose and silicon dioxide. As the binders, there may be used, for example, polyvinyl alcohol, polyvinyl ether, ethylcellulose, methylcellulose, acacia, tragacanth, gelatin, shellac, hydroxypropylcellulose, hydroxypropylstarch and polyvinylpyrrolidone. As the disintegrators, there may be used, for example, starch, agar, gelatin powder, crystalline cellulose, calcium carbonate, sodium hydrogencarbonate, calcium citrate, dextrin and pectin. As the lubricants, there may be used, for example, magnesium stearate, talc, polyethylene glycol, silica and hardened vegetable oils. As the colorants, there may be used those allowed as colorants for medicines. As the corrigents, there may be used, for example, cocoa powder, menthol, aromatic powder, peppermint oil, borneol and cinnamon powder. As a matter of course, these tablets and granules may be coated suitably with sugar, gelatin or the like.

In the preparation of an injectable liquid, if necessary, a pH regulator, buffer agent, stabilizer, preservative, solubilizer and suspending agent are added to the active ingredient, and a subcutaneous, intramuscular or a intravenous injectable liquid is prepared from the mixture.

The following examples will further illustrate the present invention, which by no means limit the invention.

EXAMPLE 1

N-(E- and Z-3,7-dimethyl-2,6-octadienoyl)dopamine 17 g of E- and Z-3,7-dimethyl-2,6-octadienoic acid was dissolved in 100 ml of anhydrous benzene. 20 ml of thionyl chloride was added to the solution and the mixture was heated under reflux. After 30 min, benzene and excessive thionyl chloride were distilled off under reduced pressure.

Then, 19 g of dopamine hydrochloride was dissolved in 100 ml of dimethylformamide (DMF) and 15 ml of triethylamine was added to the solution. The acid chloride obtained as above was added dropwise to this solution under stirring and cooling with ice. After carrying out the reaction for 1 h, the reaction mixture was added to ice-water and extracted with 200 ml of ether. After washing with water, the extract was dried over anhydrous magnesium sulfate and concentrated under reduced pressure. The concentrated product was crystallized from benzene to obtain 20 g of the intended compound, i.e. N-(E- and Z-3,7-dimethyl-2,6-octadienoyl)-dopamine as white needle-like crystals.

M.p.: 103.5°–104.5° C.

Elementary analysis as $C_{18}H_{25}NO_3$:

|  | C | H | N |
| --- | --- | --- | --- |
| Calculated (%) | 71.25 | 8.31 | 4.62 |
| Found (%) | 71.24 | 8.32 | 4.64 |

NMR (CDCl$_3$, δ): 6.8–7.1 (broad, 2H), 6.4–6.9 (m, 3H), 5.80 (m, 1H), 5.54 (m, 1H), 5.10 (m, 1H), 3.42 (m, 2H), 2.65 (m, 2H), 1.80–2.30 (m, 4H), 1.80, 1.68, 1.60 (s, 9H).

EXAMPLE 2

N-[(E,E,E)- and (Z.E.E.)-3,7,11,15-tetramethyl-2,6,10,14-hexadecatetraenoyl]dopamine 7.1 g of (E,E,E)- and (Z,E,E)-3,7,11,15-tetramethyl-2,6,10,14-hexadecatetraenoic acid was dissolved in 200 ml of anhydrous ether. 10 ml of triethylamine was added to the solution. 3 g of ethyl chlorocarbonate was added dropwise to the mixture under stirring and cooling with ice. After carrying out the reaction for 1 hour, the reaction mixture was poured in iced water. The organic layer was washed with dilute hydrochloric acid and then with water, dried over anhydrous magnesium sulfate and concentrated under reduced pressure. 5.7 g of dopamine hydrochloride was dissolved in 50 ml of dimethylformamide. 10 ml of triethylamine was added to the solution. The acid anhydride obtained as above was added dropwise to this solution at room temperature. After carrying out the reaction for 1 h, the reaction mixture was poured in ice-water and extracted with 200 ml of ether. The extract was washed with water, dried over anhydrous magnesium sulfate and concentrated under reduced pressure. The concentrate was purified according to silica gel column chromatography to obtain 5.2 g of the intended compound, i.e., N-[(E,E,E)- and (Z,E,E)-3,7,11,15-tetramethyl-2,6,10,14-hexadecatetraenoyl]dopamine, as colorless oily product.

Elementary analysis as C$_{28}$H$_{41}$NO$_3$:

| | C | H | N |
|---|---|---|---|
| Calculated (%) | 76.49 | 9.40 | 3.19 |
| Found (%) | 76.50 | 9.40 | 3.18 |

NMR (CDCl$_3$, δ): 6.8–7.2 (broad, 2H), 6.4–6.8 (m, 3H), 5.80 (m, 1H), 5.54 (m, 1H), 5.10 (m, 3H), 3.42 (m, 2H), 2.65 (m, 2H), 1.80–2.30 (m, 12H), 1.80, 1.68, 1.60 (s, 15H).

EXAMPLES 3 TO 6

Compounds shown in Table 1 were synthesized in the same manner as in Example 1 or 2.

TABLE 1

| Example | n | Molecular formula | | Elementary analysis | | | NMR (CDCl$_3$, δ) |
|---|---|---|---|---|---|---|---|
| | | | | C (%) | H (%) | N (%) | |
| 3 | 2 | C$_{23}$H$_{33}$NO$_3$ | Calcd. | 74.36 | 8.95 | 3.77 | 6.8~7.1 (broad, 2H), 6.4~6.9 (m, 3H), |
| | | | Found | 74.33 | 8.94 | 3.79 | 5.80 (m, 1H), 5.54 (m, 1H), 5.10 (m, 2H) |
| | | | | | | | 3.42 (m, 2H), 2.65 (m, 2H), |
| | | | | | | | 1.80~2.30 (m, 8H), 1.80, 1.68, 1.60 (s, 12H) |
| 4 | 4 | C$_{33}$H$_{49}$NO$_3$ | Calcd. | 78.06 | 9.73 | 2.76 | 6.8~7.2 (broad, 2H), 6.4~6.8 (m, 3H), |
| | | | Found | 78.05 | 9.74 | 2.75 | 5.80 (m, 1H), 5.54 (m, 1H), 5.10 (m, 4H), |
| | | | | | | | 3.42 (m, 2H), 2.65 (m, 2H), 1.80~2.30 |
| | | | | | | | (m, 16H), 1.80, 1.68, 1.60 (s, 18H) |
| 5 | 5 | C$_{38}$H$_{58}$NO$_3$ | Calcd. | 79.25 | 9.98 | 2.43 | 6.8~7.2 (broad, 2H), 6.4~6.8 (m, 3H), |
| | | | Found | 79.25 | 9.98 | 2.42 | 5.80 (m, 1H), 5.54 (m, 1H), 5.10 (m, 5H), |
| | | | | | | | 3.42 (m, 2H), 2.65 (m, 2H), 1.80~2.30 |
| | | | | | | | (m, 20H), 1.80, 1.68, 1.60 (s, 21H) |
| 6 | 6 | C$_{43}$H$_{65}$NO$_3$ | Calcd. | 80.20 | 10.17 | 2.18 | 6.8~7.2 (broad, 2H), 6.4~6.8 (m, 3H), |
| | | | Found | 80.20 | 10.16 | 2.17 | 5.80 (m, 1H), 5.54 (m, 1H), 5.10 (m, 6H), |
| | | | | | | | 3.42 (m, 2H), 2.65 (m, 2H), 1.80~2.30 |
| | | | | | | | (m, 24H), 1.80, 1.68, 1.60 (s, 24H) |

EXAMPLE 7

Methyl-N-[(E,E,E)- and (Z,E,E)-3,7,11,15-tetramethyl-2,6,10,14-hexadecatetraenoyl]-L-dopa 6.1 g of (E,E,E)- and (Z,E,E)-3,7,11,15-tetramethyl-2,6,10,14-hexadecatetraenoic acid was dissolved in 100 ml of anhydrous benzene. 10 ml of thionyl chloride was added to the solution and the mixture was heated under reflux. After 30 min, benzene and excessive thionyl chloride were distilled off under reduced pressure. 5 g of methyl-L-dopa hydrochloride was dissolved in 100 ml of dimethylformamide and 10 ml of triethylamine was added to the solution. The acid chloride obtained as above was added dropwise to this solution under stirring and cooling with ice. After carrying out the reaction for 1 h, the reaction mixture was poured into ice-water and extracted with 200 ml of ether. The extract was washed with water, dried over anhydrous magnesium sulfate and concentrated under reduced pressure. The resulting concentrate was purified according to silica gel chromatography to obtain 4.6 g of the intended compound, i.e., methyl-N-[(E,E,E)- and (Z,E,E)-3,7,11,15-tetramethyl-2,6,10,14-hexadecatetraenoyl]-L-dopa.

Elementary analysis as C$_{35}$H$_{51}$NO$_5$:

| | C | H | N |
|---|---|---|---|
| Calculated (%) | 74.30 | 9.09 | 2.48 |
| Found (%) | 74.29 | 9.10 | 2.48 |

NMR (CDCl$_3$, δ): 6.9–7.2 (broad, 2H), 6.3–6.8 (m, 3H), 6.02 (d, 1H, J=8 Hz), 5.58 (m, 1H), 5.10 (m, 4H), 4.85 (m, 1H), 3.72 (s, 3H), 3.00 (d, 2H, J=6 Hz), 1.80–2.30 (m, 16H), 1.79, 1.65, 1.60 (s, 18H).

EXAMPLES 8 TO 12

Compounds shown in Table 2 were synthesized in the same manner as in Example 7.

TABLE 2

| Example | n | Molecular formula | Elementary analysis | | | NMR (CDCl$_3$, δ) |
|---|---|---|---|---|---|---|
| | | | | C (%) | H (%) | N (%) | |
| 8 | 1 | C$_{19}$H$_{27}$NO$_5$ | Calcd. | 66.46 | 7.53 | 3.88 | 6.9~7.2 (broad, 2H), 6.3~6.8 (m, 3H), 6.00 (d, 1H, J = 8 Hz), |
| | | | Found | 66.45 | 7.53 | 3.90 | 5.56 (m, 1H), 5.10 (m, 1H), 4.84 (m, 1H), 3.70 (s, 3H), |
| | | | | | | | 2.98 (d, 2H, J = 6 Hz), 1.80~2.30 (m, 4H), |
| | | | | | | | 1.79, 1.65, 1.60 (s, 9H) |
| 9 | 2 | C$_{25}$H$_{35}$NO$_5$ | Calcd. | 69.90 | 8.21 | 3.26 | 6.9~7.2 (broad, 2H), 6.3~6.8 (m, 3H), 6.00 (d, 1H, J = 8 Hz), |
| | | | Found | 69.90 | 8.20 | 3.24 | 5.56 (m, 1H), 5.10 (m, 2H), 4.84 (m, 1H), 3.70 (s, 3H), |
| | | | | | | | 3.00 (d, 2H, J = 6 Hz), 1.80~2.30 (m, 8H), |
| | | | | | | | 1.79, 1.65, 1.60 (s, 12H) |
| 10 | 3 | C$_{30}$H$_{45}$NO$_5$ | Calcd. | 72.40 | 8.71 | 2.81 | 6.9~7.2 (broad, 2H), 6.3~6.8 (m, 3H), 6.02 (d, 1H, J = 8 Hz), |
| | | | Found | 72.38 | 8.71 | 2.80 | 5.56 (m, 1H), 5.10 (m, 3H), 4.85 (m, 1H), 3.70 (s, 3H), |
| | | | | | | | 3.00 (d, 2H, J = 6 Hz), 1.80~2.30 (m, 12H), |
| | | | | | | | 1.79, 1.65, 1.60 (s, 15H) |
| 11 | 5 | C$_{14}$H$_{50}$NO$_5$ | Calcd. | 75.79 | 9.38 | 2.21 | 6.9~7.2 (broad, 2H), 6.3~6.8 (m, 3H), 6.02 (d, 1H, J = 8 Hz), |
| | | | Found | 75.80 | 9.38 | 2.19 | 5.59 (m, 1H), 5.10 (m, 5H), 4.85 (m, 1H), 3.72 (s, 3H), |
| | | | | | | | 3.00 (d, 2H, J = 6 Hz), 1.80~2.30 (m, 20H), |
| | | | | | | | 1.79, 1.65, 1.60 (s, 21H) |
| 12 | 6 | C$_{45}$H$_{67}$NO$_5$ | Calcd. | 76.99 | 9.62 | 2.00 | 6.9~7.2 (broad, 2H), 6.3~6.8 (m, 3H), 6.02 (d, 1H, J = 8 Hz), |
| | | | Found | 76.98 | 9.63 | 2.01 | 5.58 (m, 1H), 5.10 (m, 6H), 4.85 (m, 1H), 3.72 (s, 3H), |
| | | | | | | | 3.00 (d, 2H, J = 6 Hz), 1.80~2.30 (m, 24H), |
| | | | | | | | 1.79, 1.65, 1.60 (s, 24H) |

EXAMPLE 13

N-[(E,E)- and (E,Z)-3,7,11-trimethyl-2,6,10-undecatrienoyl]-l-epinephrine 7.4 g of (E,E)- and (E,Z)-3,7,11-trimethyl-2,6,10-undecatrienoic acid was dissolved in 200 ml of anhydrous ether. 10 ml of triethylamine was added to the solution and then 5 g of ethyl chlorocarbonate was added dropwise thereto under stirring under cooling. After carrying out the reaction for 1 h, the reaction mixture was poured into iced water. An organic layer was washed with dilute hydrochloric acid and then with water, dried over anhydrous magnesium sulfate and concentrated under reduced pressure.

Ten grams of epinephrine bitartrate was suspended in HMPA and 10 ml of water and 18 ml of triethylamine were added to the suspension. The acid anhydride obtained as above was added dropwise to this mixture at room temperature. After carrying out the reaction for 1 h, the reaction mixture was poured into ice-water and then extracted with 200 ml of ether. The extract was washed with water, dried over anhydrous magnesium sulfate and concentrated under reduced pressure. The concentrate was purified according to silica gel column chromatography to obtain 5.5 g of the intended compound, i.e., N-[(E,E)- and (E,Z)-3,7,11-trimethyl-2,6,10-undecatrienoyl]-l-epinephrine.

Elementary analysis as C$_{24}$H$_{35}$NO$_4$:

| | C | H | N |
|---|---|---|---|
| Calculated (%) | 71.79 | 8.79 | 3.49 |
| Found (%) | 71.80 | 8.79 | 3.50 |

NMR (CDCl$_3$, δ): 6.5–6.9 (broad, 2H), 6.7–7.0 (m, 3H), 5.74, 5.50 (m, 1H), 5.10 (m, 2H), 4.93 (m, 1H), 3.2–3.9 (m, 2H), 2.92 (s, 3H), 1.8–2.3 (m, 9H), 1.76, 1.69, 1.59 (s, 12H).

EXAMPLES 14 TO 18

Compounds shown in Table 3 were obtained using corresponding carboxylic acids in the same manner as in Example 13.

EXAMPLES 19 TO 30

Compounds shown in Tables 4 and 5 were obtained using l-norepinephrine tartrate and dl-isoproterenol hydrochloride in the same manner as in Example 13.

TABLE 3

| Example | n | Molecular formula | Elementary analysis | | | NMR (CDCl$_3$, δ) |
|---|---|---|---|---|---|---|
| | | | | C (%) | H (%) | N (%) | |
| 14 | 1 | C$_{19}$H$_{27}$NO$_4$ | Calcd. | 68.44 | 8.16 | 4.20 | 6.5~6.9 (broad, 2H), 6.7~7.0 (m, 3H), 5.74~5.50 (m, 1H), |
| | | | Found | 68.44 | 8.16 | 4.22 | 5.10 (m, 1H), 4.92 (m, 1H), 3.2~3.9 (m, 2H), |
| | | | | | | | 2.92 (s, 3H), 1.80~2.30 (m, 5H), 1.76, 1.68, |

TABLE 3-continued

| Example | n | Molecular formula | Elementary analysis | | C (%) | H (%) | N (%) | NMR (CDCl$_3$, δ) |
|---|---|---|---|---|---|---|---|---|
| 15 | 3 | C$_{29}$H$_{13}$NO$_3$ | Calcd. | | 74.16 | 9.23 | 2.98 | 1.58 (s, 9H)<br>6.5~6.9 (broad, 2H), 6.7~7.0 (m, 3H), 5.74, 5.50 |
|  |  |  | Found | | 74.15 | 9.24 | 2.96 | (m, 1H), 5.10 (m, 3H), 4.93 (m, 1H), 3.2~3.9<br>(m, 2H), 2.92 (s, 3H), 1.8~2.3 (m, 13H),<br>1.76, 1.69, 1.60 (s, 15H) |
| 16 | 4 | C$_{34}$H$_{51}$NO$_4$ | Calcd. | | 75.93 | 9.56 | 2.60 | 6.5~6.9 (broad, 2H), 6.7~7.0 (m, 3H), 5.74, 5.50 |
|  |  |  | Found | | 75.93 | 9.56 | 2.59 | (m, 1H), 5.10 (m, 4H), 4.93 (m, 1H), 3.2~3.9<br>(m, 2H), 2.92 (s, 3H), 1.8~2.3 (m, 17H),<br>1.76, 1.68, 1.58 (s, 18H) |
| 17 | 5 | C$_{30}$H$_{50}$NO$_4$ | Calcd. | | 77.31 | 8.21 | 2.31 | 6.5~6.9 (broad, 2H), 6.7~7.0 (m, 3H), 5.74, 5.50 |
|  |  |  | Found | | 77.32 | 9.82 | 2.29 | (m, 1H), 5.10 (m, 5H), 4.92 (m, 1H), 3.2~3.9<br>(m, 2H), 2.91 (s, 3H), 1.8~2.3 (m, 21H),<br>1.77, 1.69, 1.60 (s, 21H) |
| 18 | 6 | C$_{44}$H$_{67}$NO$_4$ | Calcd. | | 78.41 | 10.02 | 2.08 | 6.5~6.9 (broad, 2H), 6.7~7.0 (m, 3H), 5.74, 5.50 |
|  |  |  | Found | | 78.40 | 10.21 | 2.09 | (m, 1H), 5.10 (m, 6H), 4.92 (m, 1H), 3.2~3.9<br>(m, 2H), 2.90 (s, 3H), 1.8~2.3 (m, 25H),<br>1.78, 1.69, 1.60 (s, 24H) |

TABLE 4

| Example | n | Molecular formula | Elementary analysis | | C (%) | H (%) | N (%) | NMR (CDCl$_3$, δ) |
|---|---|---|---|---|---|---|---|---|
| 19 | 1 | C$_{18}$H$_{25}$NO$_4$ | Calcd. | | 67.69 | 7.89 | 4.39 | 6.7~7.8 (broad, 2H), 6.4~6.8 (m, 3H), 6.42 (broad, 1H), |
|  |  |  | Found | | 67.68 | 7.88 | 4.41 | 5.54 (m, 1H), 5.10 (m, 1H), 4.52 (m, 1H), 3.36 (m, 2H),<br>1.8~2.3 (m, 5H), 1.78, 1.68, 1.60 (s, 9H) |
| 20 | 2 | C$_{23}$H$_{33}$NO$_4$ | Calcd. | | 71.29 | 8.58 | 3.61 | 6.7~7.2 (broad, 2H), 6.4~6.8 (m, 3H), 6.40 (broad, 1H), |
|  |  |  | Found | | 71.30 | 8.58 | 3.61 | 5.54 (m, 1H), 5.10 (m, 2H), 4.53 (m, 1H), 3.35 (m, 2H),<br>1.8~2.3 (m, 9H), 1.78, 1.68, 1.60 (s, 12H) |
| 21 | 3 | C$_{28}$H$_{41}$NO$_4$ | Calcd. | | 73.81 | 9.07 | 3.07 | 6.8~7.5 (broad, 2H), 6.4~6.8 (m, 3H), 6.41 (broad, 1H), |
|  |  |  | Found | | 73.80 | 9.07 | 3.09 | 5.54 (m, 1H), 5.10 (m, 3H), 4.53 (m, 1H), 3.36 (m, 2H),<br>1.8~2.3 (m, 13H), 1.78, 1.68, 1.60 (s, 15H) |
| 22 | 4 | C$_{33}$H$_{40}$NO$_4$ | Calcd. | | 75.67 | 9.43 | 2.67 | 6.8~7.5 (broad, 2H), 6.4~6.8 (m, 3H), 6.40 (broad, 1H), |
|  |  |  | Found | | 75.67 | 9.42 | 2.69 | 5.54 (m, 1H), 5.10 (m, 4H), 4.52 (m, 1H), 3.37 (m, 2H),<br>1.8~2.3 (m, 17H), 1.78, 1.68, 1.60 (s, 18H) |
| 23 | 5 | C$_{38}$H$_{57}$NO$_4$ | Calcd. | | 77.11 | 9.71 | 2.37 | 6.8~7.5 (broad, 2H), 6.4~6.8 (m, 3H), 6.40 (broad, 1H), |
|  |  |  | Found | | 77.10 | 9.72 | 2.37 | 5.54 (m, 1H), 5.10 (m, 5H), 4.52 (m, 1H), 3.37 (m, 2H),<br>1.8~2.3 (m, 21H), 1.78, 1.68, 1.60 (s, 21H) |
| 24 | 6 | C$_{49}$H$_{65}$NO$_4$ | Calcd. | | 78.25 | 9.93 | 2.12 | 6.8~7.5 (broad, 2H), 6.4~6.8 (m, 3H), 6.40 (broad, 1H), |
|  |  |  | Found | | 78.23 | 9.93 | 2.12 | 5.54 (m, 1H), 5.10 (m, 6H), 4.52 (m, 1H), 3.37 (m, 2H),<br>1.8~2.3 (m, 25H), 1.78, 1.68, 1.60 (s, 24H) |

TABLE 5

| Example | n | Molecular formula | Elementary analysis | | C (%) | H (%) | N (%) | NMR (CDCl$_3$, δ) |
|---|---|---|---|---|---|---|---|---|
| 25 | 1 | C$_{21}$H$_{31}$NO$_3$ | Calcd. | | 69.77 | 8.65 | 3.88 | 6.2~7.0 (broad, 2H), 6.6~7.1 (m, 3H), 5.92 (m, 1H), |
|  |  |  | Found | | 69.78 | 8.66 | 3.85 | 5.10 (m, 1H), 4.76 (m, 1H), 2.95~4.36 (m, 3H),<br>1.8~2.4 (m, 5H), 1.78, 1.68, 1.59 (s, 9H),<br>1.22, 1.04 (d, 6H, J = 7 Hz) |
| 26 | 2 | C$_{26}$H$_{30}$NO$_4$ | Calcd. | | 72.69 | 9.15 | 3.26 | 6.2~7.0 (broad, 2H), 6.6~7.1 (m, 3H), 5.92 (m, 1H), |
|  |  |  | Found | | 72.68 | 9.15 | 3.24 | 5.10 (m, 2H), 4.76 (m, 1H), 2.95~4.36 (m, 3H), |

TABLE 5-continued

| Example | n | Molecular formula | | Elementary analysis | | | NMR (CDCl$_3$, δ) |
|---|---|---|---|---|---|---|---|
| | | | | C (%) | H (%) | N (%) | |
| 27 | 3 | C$_{31}$H$_{47}$NO$_4$ | Calcd. | 74.81 | 9.52 | 2.81 | 6.2~7.0 (broad, 2H), 6.6~7.1 (m, 3H), 5.92 (m, 1H), |
| | | | Found | 74.81 | 9.52 | 2.83 | 5.10 (m, 3H), 4.76 (m, 1H), 2.95~4.36 (m, 3H), |
| | | | | | | | 1.8~2.4 (m, 13H), 1.78, 1.68, 1.60 (s, 15H), |
| | | | | | | | 1.22, 1.04 (d, 6H, J = 7 Hz) |
| 28 | 4 | C$_{30}$H$_{55}$NO$_4$ | Calcd. | 76.41 | 9.80 | 2.48 | 6.2~7.0 (broad, 2H), 6.6~7.1 (m, 3H), 5.92 (m, 1H), |
| | | | Found | 76.42 | 9.80 | 2.48 | 5.10 (m, 4H), 4.76 (m, 1H), 2.95~4.36 (m, 3H), |
| | | | | | | | 1.8~2.4 (m, 17H), 1.78, 1.68, 1.60 (s, 18H), |
| | | | | | | | 1.22, 1.04 (d, 6H, J = 7 Hz) |
| 29 | 5 | C$_{41}$H$_{63}$NO$_4$ | Calcd. | 77.68 | 10.02 | 2.21 | 6.2~7.0 (broad, 2H), 6.6~7.1 (m, 3H), 5.92 (m, 1H) |
| | | | Found | 77.69 | 10.03 | 2.19 | 5.10 (m, 5H), 4.76 (m, 1H), 2.95~4.36 (m, 3H), |
| | | | | | | | 1.8~2.4 (m, 21H), 1.78, 1.68, 1.60 (s, 21H), |
| | | | | | | | 1.22, 1.04 (d, 6H, J = 7 Hz) |
| 30 | 6 | C$_{46}$H$_{71}$NO$_4$ | Calcd. | 78.68 | 10.19 | 2.00 | 6.2~7.0 (broad, 2H), 6.6~7.1 (m, 3H), 5.92 (m, 1H) |
| | | | Found | 78.70 | 10.19 | 2.01 | 5.10 (m, 6H), 4.67 (m, 1H), 2.95~4.36 (m, 3H), |
| | | | | | | | 1.8~2.4 (m, 25H), 1.78, 1.68, 1.60 (s, 24H), |
| | | | | | | | 1.22, 1.04 (d, 6H, J = 7 Hz) |

The embodiments of the invention in which an exclusive property or privilege is claimed are defined as follows:

1. Polyprenylcarboxylic acid amides of the general formula:

wherein R$^1$ represents a hydrogen atom or a lower alkyl group, R$^2$ represents a hydrogen atom or a group of the formula: —COOR$^4$ in which R$^4$ represents a lower alkyl group, R$^3$ represents a hydrogen atom or an OH group and n represents an integer of 1 to 6.

2. Polyprenylcarboxylic acid amides according to claim 1 wherein R$^1$, R$^2$ and R$^3$ represent a hydrogen atom and n represents an integer of 1 to 6.

3. Polyprenylcarboxylic acid amides according to claim 1 wherein R$^1$ represents a hydrogen atom, R$^2$ represents —COOCH$_3$, R$^3$ represents a hydrogen atom and n represents an integer of 1 to 6.

4. Polyprenylcarboxylic acid amides according to claim 1 wherein R$^1$ represents a methyl group, R$^2$ represents a hydrogen atom, R$^3$ represents a hydroxyl group and n represents an integer of 1 to 6.

5. Polyprenylcarboxylic acid amides according to claim 1 wherein R$^1$ and R$^2$ represent each a hydrogen atom, R$^3$ represents a hydroxyl group and n represents an integer of 1 to 6.

6. Polyprenylcarboxylic acid amides according to claim 1 wherein R$^1$ represents an isopropyl group, R$^2$ represents a hydrogen atom, R$^3$ represents a hydroxyl group and n represents an integer of 1 to 6.

* * * * *